United States Patent
Eddy

(10) Patent No.: US 10,967,082 B2
(45) Date of Patent: Apr. 6, 2021

(54) METHOD OF LIMITING THE SPREAD OF NOROVIRUS WITHIN A CRUISE SHIP

(71) Applicant: Parasol Medical LLC, Buffalo Grove, IL (US)

(72) Inventor: Patrick E. Eddy, Allendale, MI (US)

(73) Assignee: PARASOL MEDICAL, LLC, Buffalo Grove, IL (US)

( * ) Notice: Subject to any disclaimer, the term of this patent is extended or adjusted under 35 U.S.C. 154(b) by 230 days.

(21) Appl. No.: 15/807,157

(22) Filed: Nov. 8, 2017

(65) Prior Publication Data

US 2019/0134244 A1    May 9, 2019

(51) Int. Cl.
     *A61L 2/18*         (2006.01)
     *A01N 25/02*      (2006.01)
     *A01N 55/00*      (2006.01)

(52) U.S. Cl.
     CPC .............. *A61L 2/18* (2013.01); *A01N 25/02* (2013.01); *A01N 55/00* (2013.01); *A61L 2202/25* (2013.01)

(58) Field of Classification Search
     CPC ....... A61L 2/18; A61L 2202/25; A01N 25/02; A01N 55/00; A01N 31/02; A01N 33/12
     See application file for complete search history.

(56) References Cited

U.S. PATENT DOCUMENTS

| 4,372,303 | A | 2/1983 | Grossmann et al. |
| 4,865,844 | A | 9/1989 | Blank et al. |

(Continued)

FOREIGN PATENT DOCUMENTS

| EP | 0108853 A1 | 5/1984 |
| EP | 2377400 A1 | 10/2011 |

(Continued)

OTHER PUBLICATIONS

Federal Institute of Industrial Property, "The International Search Report and the Written Opinion of the International Searching Authority," dated Jan. 24, 2019 (9 pages).

(Continued)

*Primary Examiner* — Regina M Yoo
(74) *Attorney, Agent, or Firm* — Price Heneveld LLP

(57) ABSTRACT

A method of limiting the spread of the norovirus within a cruise ship comprising: identifying a surface within a common area of a cruise ship that passengers are likely to touch; and applying a silane quaternary ammonium ion or salt thereof to the surface. The common area can be an elevator and the surface an elevator button. The common area can be a stairway and the surface a handrail. The common area can be a casino. The common area can be a dining room. The common area can be a walkway and the surface a handrail. The silane quaternary ammonium ion or salt thereof can be 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. Applying the silane quaternary ammonium ion or salt thereof to the surface comprises applying a solution including the silane quaternary ammonium ion or salt thereof and a solvent.

14 Claims, 8 Drawing Sheets

(56) References Cited

U.S. PATENT DOCUMENTS

| | | | |
|---|---|---|---|
| 4,921,691 A | 5/1990 | Stockel | |
| 5,079,004 A | 1/1992 | Blank et al. | |
| 5,183,664 A | 2/1993 | Ansell | |
| 5,270,358 A | 12/1993 | Asmus | |
| 5,428,078 A | 6/1995 | Cohen et al. | |
| 5,762,623 A | 6/1998 | Murphy et al. | |
| 5,954,869 A | 9/1999 | Elfersy et al. | |
| 5,959,014 A | 9/1999 | Liebeskind et al. | |
| 6,224,579 B1 | 5/2001 | Modak et al. | |
| 6,495,229 B1 | 12/2002 | Carte et al. | |
| 6,821,943 B2 | 11/2004 | Avery et al. | |
| 6,994,890 B2 | 2/2006 | Ohlhausen et al. | |
| 7,045,673 B1 | 5/2006 | Batich et al. | |
| 7,704,313 B2 | 4/2010 | Ohlhausen et al. | |
| 7,709,694 B2 | 5/2010 | Batich et al. | |
| 7,754,004 B2 | 7/2010 | Ohlhausen et al. | |
| 7,790,217 B2 | 9/2010 | Toreki et al. | |
| 8,025,120 B2 | 9/2011 | Eddy | |
| 8,257,780 B2 | 9/2012 | Ohlhausen et al. | |
| 8,440,217 B1 | 5/2013 | El-Naggar et al. | |
| 8,491,922 B2 | 7/2013 | Eddy | |
| 8,574,844 B2* | 11/2013 | Burkhardt, III | C12Q 1/701 435/6.1 |
| 8,639,527 B2 | 1/2014 | Rensvold et al. | |
| 8,679,526 B2 | 3/2014 | Van Den Plas et al. | |
| 9,028,846 B2 | 5/2015 | Eddy | |
| 9,433,708 B2 | 9/2016 | Eddy | |
| 9,675,735 B2 | 6/2017 | Eddy | |
| 9,717,249 B2 | 8/2017 | Eddy | |
| 9,757,769 B2* | 9/2017 | Grossman | D06M 13/51 |
| 9,840,626 B2* | 12/2017 | Farrugia | C09D 11/30 |
| 9,855,584 B2* | 1/2018 | Grossman | B05D 5/00 |
| 2002/0111282 A1 | 8/2002 | Charaf et al. | |
| 2007/0021383 A1 | 1/2007 | Loder | |
| 2007/0042198 A1 | 2/2007 | Schonemyr et al. | |
| 2007/0218096 A1 | 9/2007 | Wooley | |
| 2007/0275929 A1* | 11/2007 | Fuls | A01N 31/02 514/75 |
| 2008/0260804 A1 | 10/2008 | Morris et al. | |
| 2009/0215917 A1 | 8/2009 | Trotter et al. | |
| 2009/0223411 A1 | 9/2009 | Higgins et al. | |
| 2009/0252647 A1 | 10/2009 | Orofino | |
| 2009/0312684 A1 | 12/2009 | Leonard et al. | |
| 2010/0028462 A1 | 2/2010 | Bolkan et al. | |
| 2010/0167978 A1 | 7/2010 | Iyer et al. | |
| 2010/0331710 A1 | 12/2010 | Eddy | |
| 2011/0124772 A1* | 5/2011 | Wang | A01N 33/12 523/177 |
| 2011/0200655 A1 | 8/2011 | Black et al. | |
| 2011/0233810 A1 | 9/2011 | Neigel et al. | |
| 2011/0236504 A1* | 9/2011 | Hata | A01N 37/44 424/618 |
| 2011/0271873 A1* | 11/2011 | Ohlhausen | A01N 33/12 106/287.11 |
| 2012/0021405 A1* | 1/2012 | Palzkill | C07K 16/10 435/5 |
| 2012/0070481 A1* | 3/2012 | Bolkan | A01N 31/12 424/404 |
| 2012/0173274 A1 | 7/2012 | Rensvold et al. | |
| 2013/0101674 A1* | 4/2013 | Toft | A01N 25/04 424/497 |
| 2013/0101677 A1 | 4/2013 | Callahan et al. | |
| 2013/0231599 A1 | 9/2013 | Eddy | |
| 2013/0273132 A1* | 10/2013 | Eddy | A01N 55/00 424/411 |
| 2013/0345170 A1 | 12/2013 | Eddy | |
| 2014/0051732 A1* | 2/2014 | Ghannoum | A01N 43/40 514/358 |
| 2014/0100504 A1 | 4/2014 | Eddy | |
| 2014/0271794 A1 | 9/2014 | Eddy | |
| 2015/0031729 A1* | 1/2015 | Ghannoum | A01N 43/40 514/358 |
| 2015/0305343 A1 | 10/2015 | Burke et al. | |
| 2015/0352320 A1* | 12/2015 | Eddy | A61M 1/285 604/29 |
| 2016/0143275 A1 | 5/2016 | Lan et al. | |
| 2016/0143276 A1 | 5/2016 | Lan et al. | |
| 2016/0171179 A1* | 6/2016 | Donofrio | G06F 16/26 705/2 |
| 2016/0262382 A1 | 9/2016 | Lan et al. | |
| 2016/0262383 A1 | 9/2016 | Lan et al. | |
| 2017/0081707 A1* | 3/2017 | Dillon | C12Q 1/689 |
| 2017/0280716 A1 | 10/2017 | Lan et al. | |

FOREIGN PATENT DOCUMENTS

| | | |
|---|---|---|
| RU | 2540478 C1 | 2/2015 |
| RU | 2599004 C1 | 10/2016 |
| WO | 0054587 A1 | 9/2000 |
| WO | 0072850 A1 | 12/2000 |
| WO | 2004087226 A1 | 10/2004 |
| WO | 2005042657 A2 | 5/2005 |
| WO | 2007061625 A2 | 5/2007 |
| WO | 2007076413 A2 | 7/2007 |
| WO | 2008076839 A2 | 6/2008 |
| WO | 2008097599 A2 | 8/2008 |
| WO | 2013102021 A2 | 7/2013 |
| WO | 2016130837 A1 | 8/2016 |

OTHER PUBLICATIONS

World Health Organization, "Guide to marine sanitation," Third Edition, 2013, pp. 90 and 147-149.

Anonymous. 2009. SiSiB PC9911 Antimicrobial. Power Chemical Corp. [online]; downloaded from URL<http://www.powerchemcorp.com/library/public/SiSiB_PC9911.pdf> on Oct. 8, 2013; 2 pages.

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

Rutala et al., "Guideline for Disinfection and Sterilization in Healthcare Facilities, 2008," Centers for Disease Control (CDC), Department of Health & Human Services, Feb. 15, 2017 (161 pages).

U.S. Food & Drug Administration (FDA), "Reprocessing Medical Devices in Health Care Settings: Validation Methods and Labeling Guidance for Industry and Food and Drug Administration Staff," Mar. 17, 2015 (44 pages).

European Commission, "Aerosol Dispensers Directive Evaluation—Background document", Sep. 23, 2016, Directorate-General for Internal Market, Industry, Entrepreneurship and SMEs, Belgium (1 page).

Monticello, Robert A., "The Use of Reactive Silane Chemistries to Provide Durable, Non-Leaching Antimicrobial Surfaces", AEGIS Environments, Midland, Michigan USA, Jan. 1, 2010 (77 pages).

AEGIS Environments, Material Safety Data Sheet AEGIS Microbe Shield(TM) Program—AEGIS(TM) Antimicrobial (Typical Application Strength), Midland, Michigan USA, May 12, 2004 (5 pages).

Jimenez et al: "Virucidal activity of a quaternary ammonium compound disinfectant against feline calicivirus: A surrogate for norovirus", AJIC: American Journal of Infection Control, vol. 34, No. 5, Jun. 1, 2006 (Jun. 1, 2006), pp. 269-273, Elsevier, Amsterdam, NL.

Anonymous: "Guidance for the Management of Norovirus Infection in Cruise Ships", •Jul. 1, 2007 (Jul. 1, 2007), pp. 1-76, Retrieved from the Internet: URL:https://virox.com/files docs/content/pdf/msds/1206520183347.pd, [retrieved on Jan. 28, 2021].

Anonymous.: "Guide to ship sanitation (third edition)", Guide to Ship Sanitation (Third Edition), World Health Organization, CH, pp. 1-171, Nov. 30, 2012 (Nov. 30, 2012), Retrieved from the Internet: URL:https://www.who.int/water sanitation health/publications/2011/ship -sanitation -guide/en/, pp. 133-135.

Extended European Search Report, European Application No. 18875379.2, dated Feb. 11, 2021 (6 pages).

\* cited by examiner

US 10,967,082 B2

METHOD OF LIMITING THE SPREAD OF NOROVIRUS WITHIN A CRUISE SHIP

BACKGROUND OF THE INVENTION

The norovirus is a virus that causes gastroenteritis. Gastroenteritis is the inflammation of the gastrointestinal tract, which includes the stomach and the small intestine. Symptoms of gastroenteritis include stomach pain, diarrhea, and vomiting. Norovirus spreads very quickly and easily, including by touching objects that have the norovirus present.

According to the United States Centers for Disease Control and Prevention (CDC), the number of outbreaks of gastroenteritis on cruise ships has increased since 2001, because of increased presence of the norovirus. The CDC even has implemented a Vessel Sanitation Program (VSP) to help cruise ships curtail outbreaks of gastroenteritis. Despite this effort, twelve cruise ships reported an outbreak of gastroenteritis caused by the norovirus in 2015. Eleven cruise ships similarly reported in 2016.

After some outbreaks, the cruise ship may undertake extensive cleaning and disinfecting. The cruise ship owners bear the cost of the cleaning and disinfecting as well as the down time.

SUMMARY OF THE INVENTION

According to an aspect of the present invention, a method of limiting the spread of norovirus within a cruise ship comprises: identifying a surface within a common area of a cruise ship that passengers are likely to touch; and applying a silane quaternary ammonium ion or salt thereof to the surface.

Embodiments of the first aspect of the invention can include any one or a combination of the following features:
the method further comprises identifying the presence of the norovirus within the cruise ship;
the method further comprises wiping the surface with a microfiber cloth;
the method further comprises testing the surface for the presence of the norovirus;
the common area is an elevator and the surface is an elevator button;
the common area is a stairway and the surface is a handrail;
the common area is a casino;
the common area is a dining room;
the common area is a walkway and the surface is a handrail;
the silane quaternary ammonium ion or salt is 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride;
applying a silane quaternary ammonium ion or salt thereof to the surface comprises applying, to the surface, a solution including the silane quaternary ammonium ion or salt thereof and a solvent;
the solvent is isopropyl alcohol;
the solution is applied via spraying the solution onto the surface with an electrostatic sprayer;
the silane quaternary ammonium ion or salt thereof is between 0.1 percent and 10 percent by weight of the solution;
the silane quaternary ammonium ion or salt thereof is between 0.75 percent and 5 percent by weight of the solution;
the silane quaternary ammonium ion or salt thereof is between 1.9 percent and 2.1 percent by weight of the solution;
the solvent is isopropyl alcohol and the isopropyl alcohol is between 30 percent to 90 percent by weight of the solution;
the isopropyl alcohol is between 55 percent and 65 percent by weight of the solution;
the method further comprises initially identifying the presence of the norovirus within the cruise ship, after spraying the solution onto the surface, wiping the surface with a microfiber cloth, and after wiping the surface with a microfiber cloth, waiting a preset period of time, and testing the surface for the presence of the norovirus.

These and other features, advantages, and objects of the present invention will be further understood and appreciated by those skilled in the art by reference to the following specification, claims, and appended drawings.

DETAILED DESCRIPTION

Figure 1:
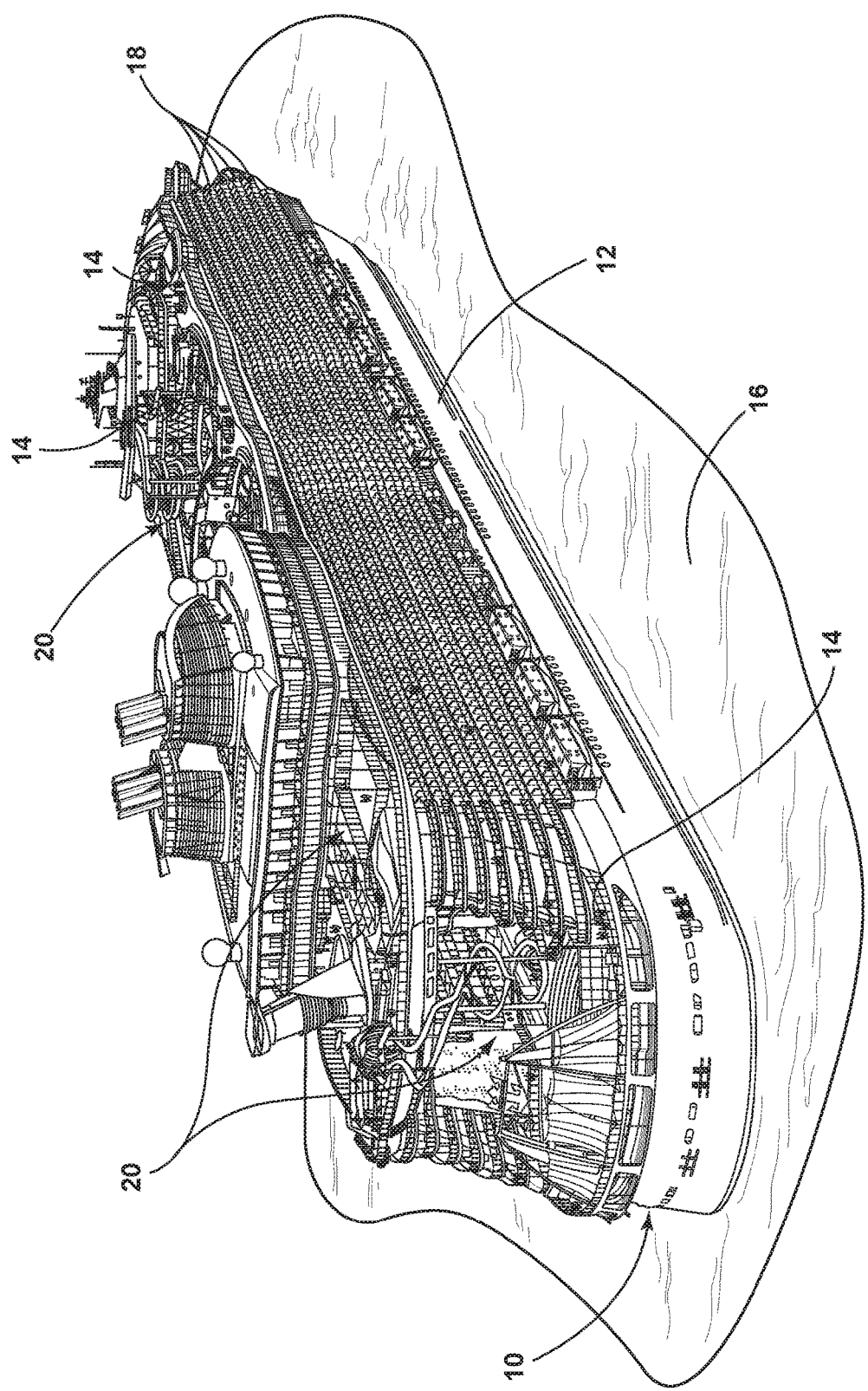
FIG. 1 is a perspective view of a cruise ship, illustrating numerous decks above a hull and passengers being transported over a body of water.
Figure 2:
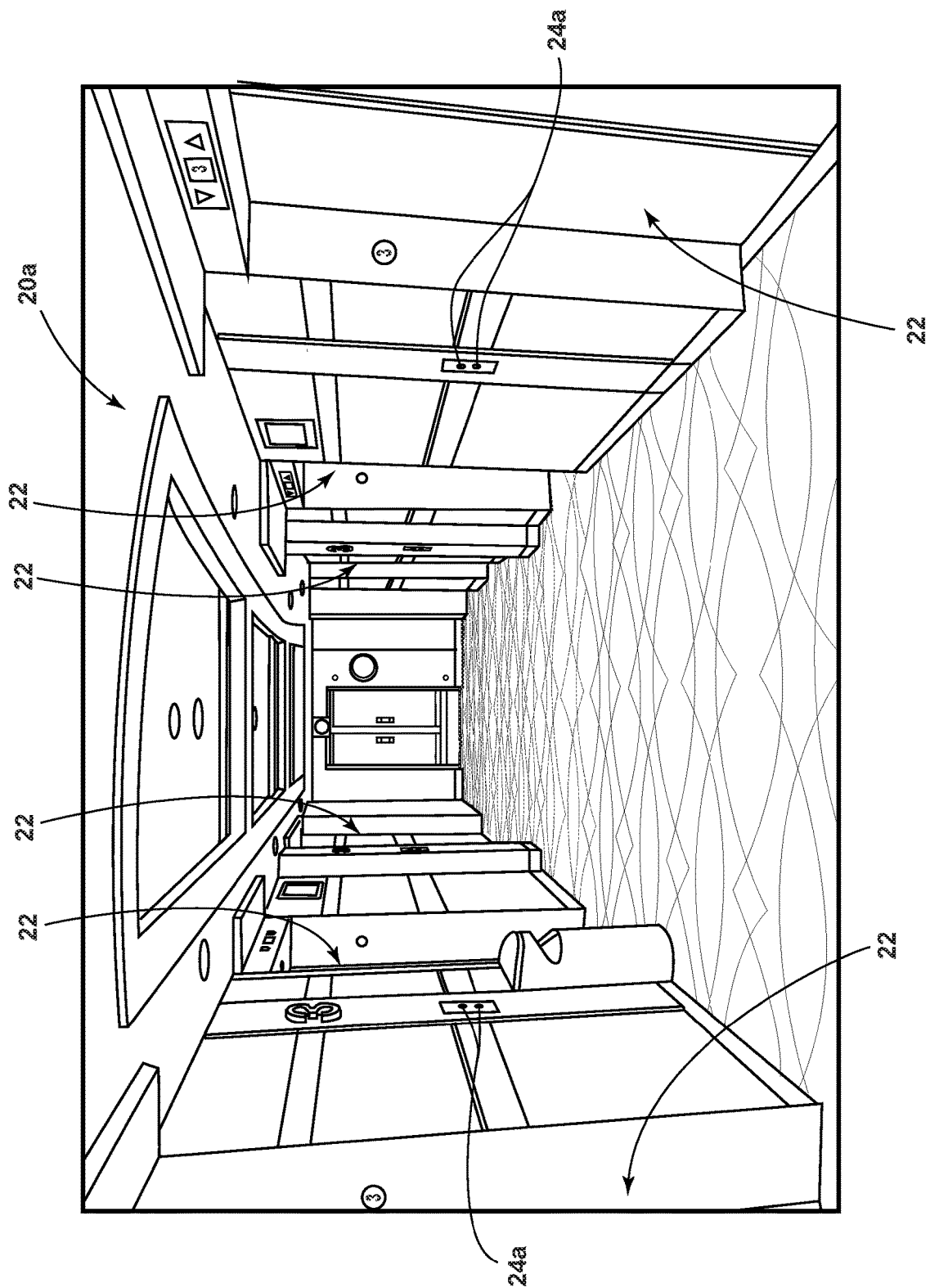
FIG. 2 is a perspective view of an elevator lobby common area and elevator buttons acting as surfaces which passengers are likely to touch.
Figure 3:
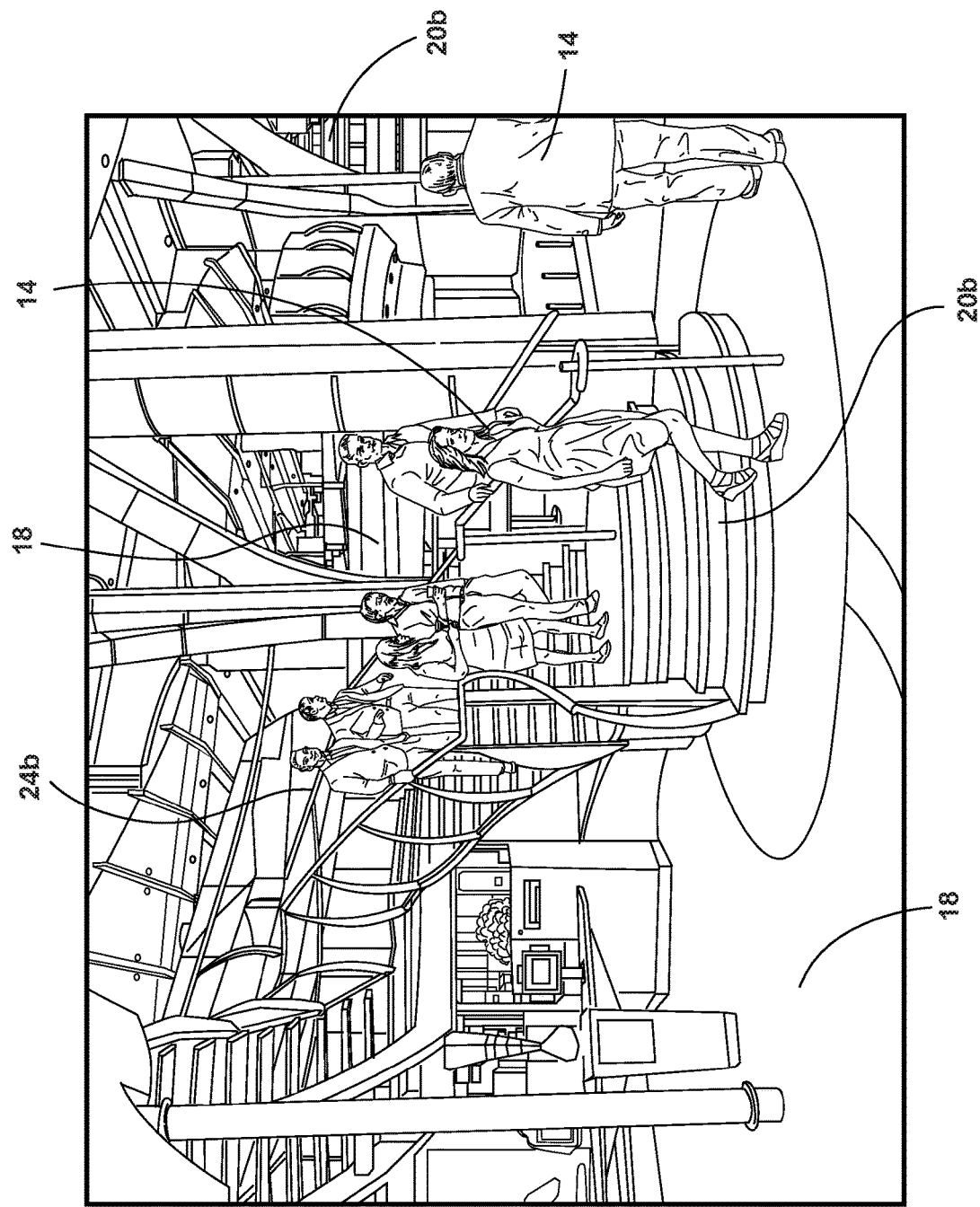
FIG. 3 is a perspective view of several stairways acting as common areas and handrails acting as surfaces which passengers are likely to touch.
Figure 4:
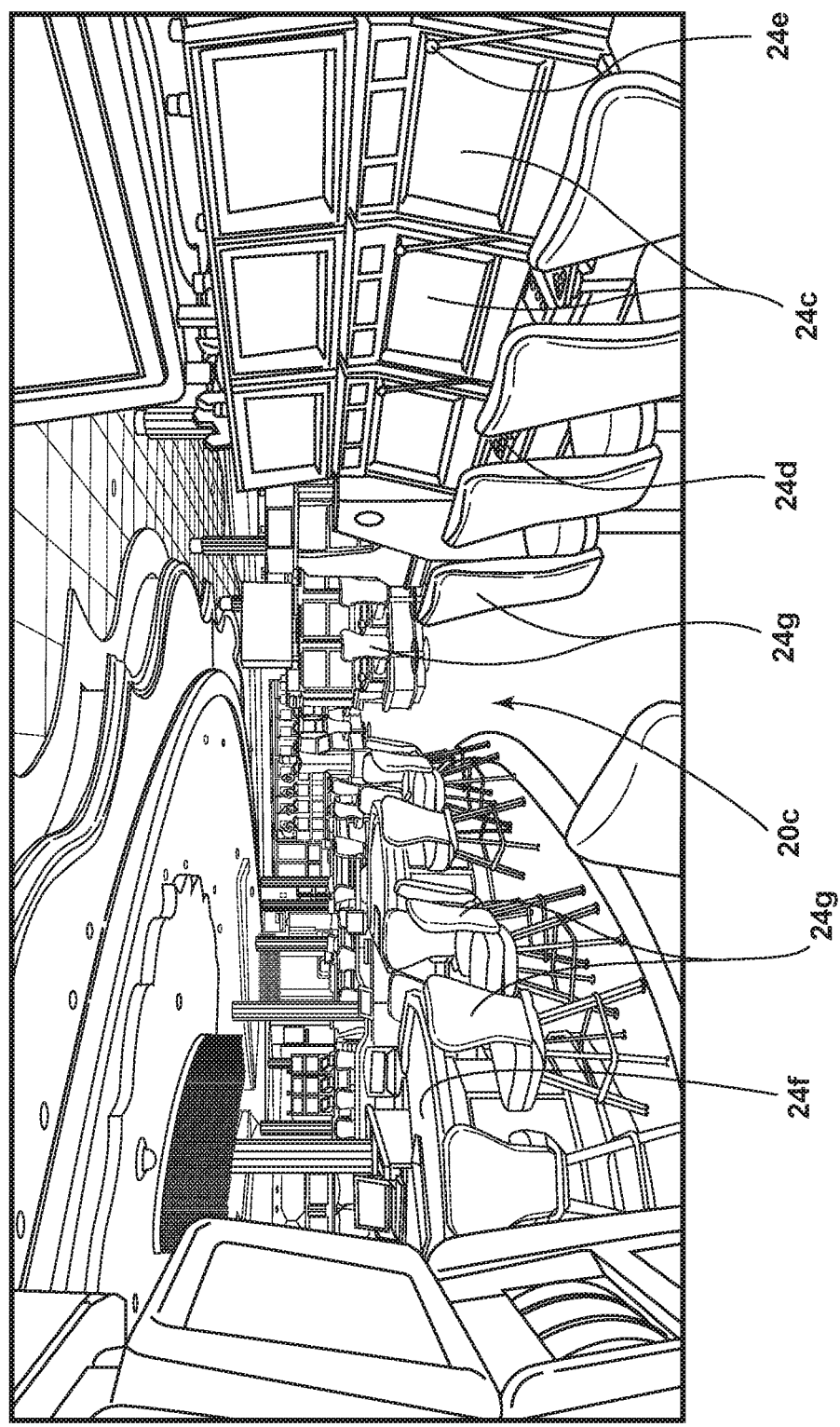
FIG. 4 is a perspective view of a casino acting as a common area for passengers and slot machine buttons acting as surfaces which passengers are likely to touch.
Figure 5:
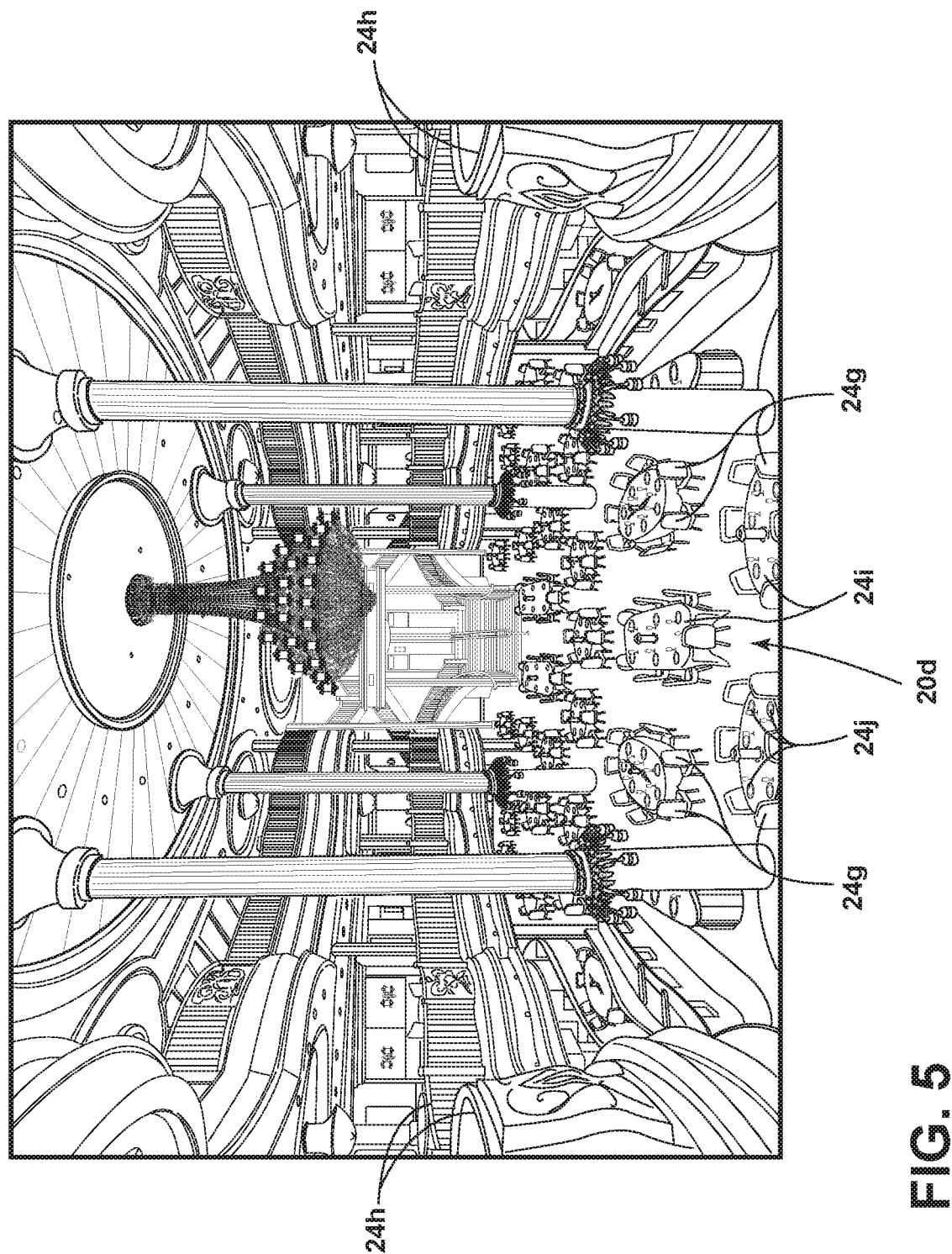
FIG. 5 is a perspective view of a dining room acting as a common area for passengers and dining table tops acting as surfaces which passengers are likely to touch.
Figure 6:
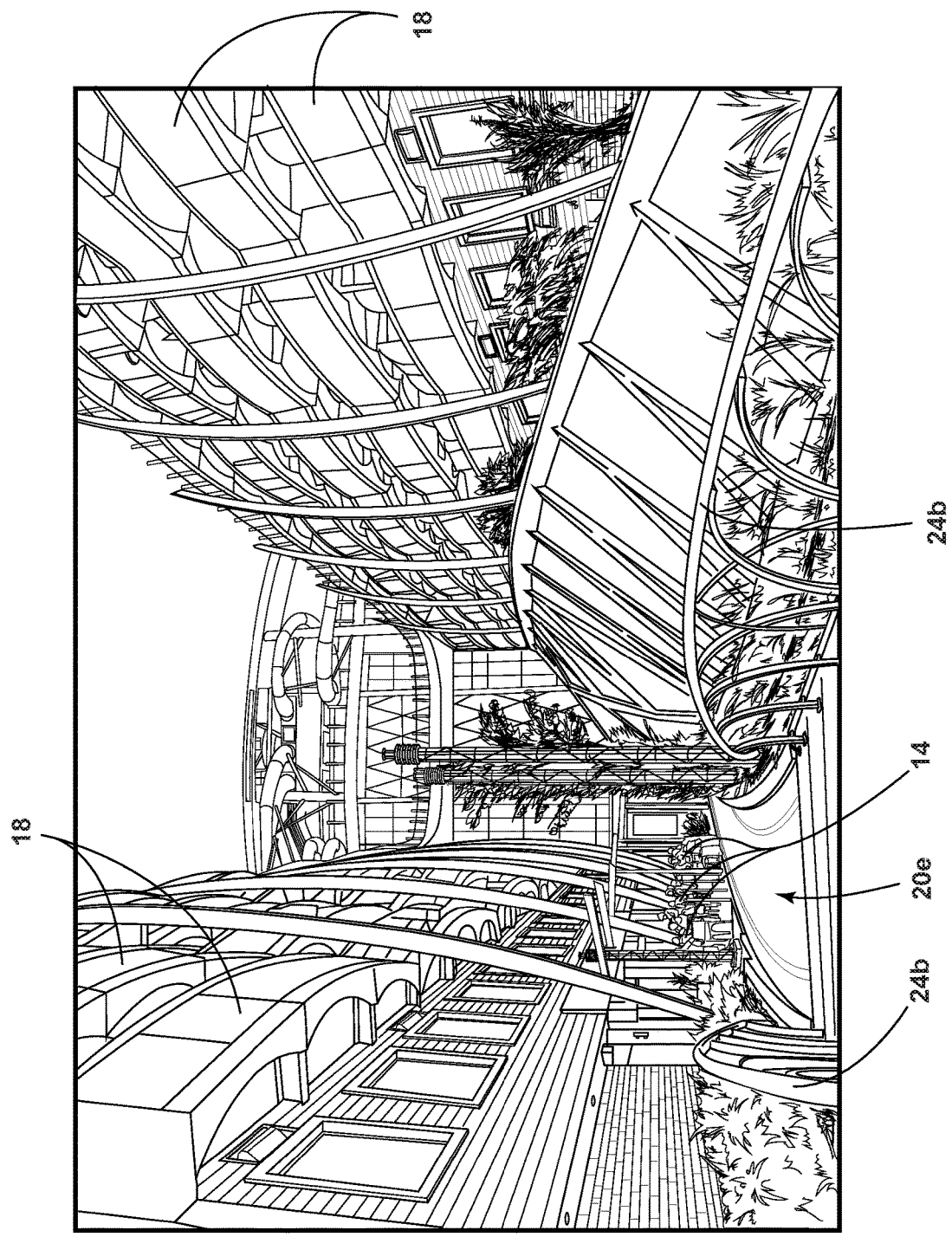
FIG. 6 is a perspective view of a walkway common area and handrails acting as surfaces which passengers are likely to touch.
Figure 7:
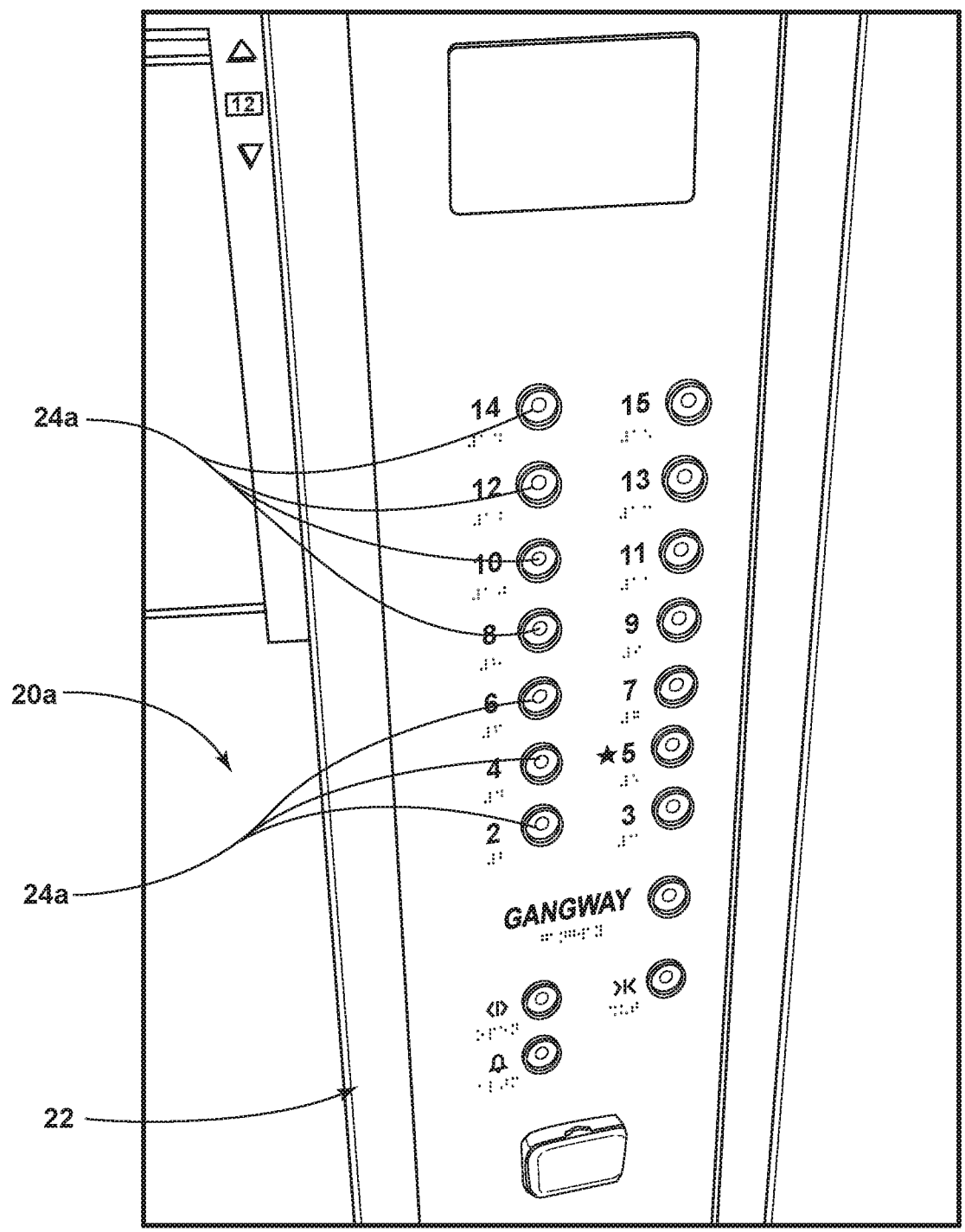
FIG. 7 is a perspective view of elevator buttons within an elevator accessible from the elevator lobby acting as surfaces which passengers are likely to touch.

Referring now to FIGS. 1-7, a cruise ship 10 includes a hull 12 configured to float on, and transport passengers 14 over, a body of water 16. The cruise ship 10 further includes one or more decks 18 within and/or above the hull 12.

The cruise ship 10 further includes one or more common areas 20, which are areas that the passengers 14 are allowed to access, on the one or more decks 18. The common areas 20 include, without limitation, an elevator lobby 20a (see FIG. 2) with elevators 22 transporting passengers 14 between the one or more decks 18, stairways 20b (see FIG. 3) on which passengers 14 can move between the one or more decks 18, a casino 20c (see FIG. 4), a dining room 20d (see FIG. 5), and a walkway 20e upon which passengers 14 walk (see FIG. 6), among other areas. The common areas 20 include surfaces 24 that the passengers 14 are likely to touch with their hands and thus constitute surfaces 24 where the norovirus can transfer from passenger 14 to passenger 14. Examples of such surfaces 24 in the common areas 20 that passengers 14 are likely to touch, include, without limitation: elevator buttons 24a in the elevator lobby 20a (see FIG. 2) and in the elevators 22 (see FIG. 7); handrails 24b for the stairways 20b (see FIG. 3); slot machine screens 24c, buttons 24d, and levers 24e, gaming table tops 24f, and seatbacks 24g in the casino 20c (see FIG. 4); railings 24h, seatbacks 24g, dining table tops 24i, and place settings 24j in the dining room 20d (see FIG. 5); and handrails 24b in the walkway 20e (see FIG. 6).

Figure 8:
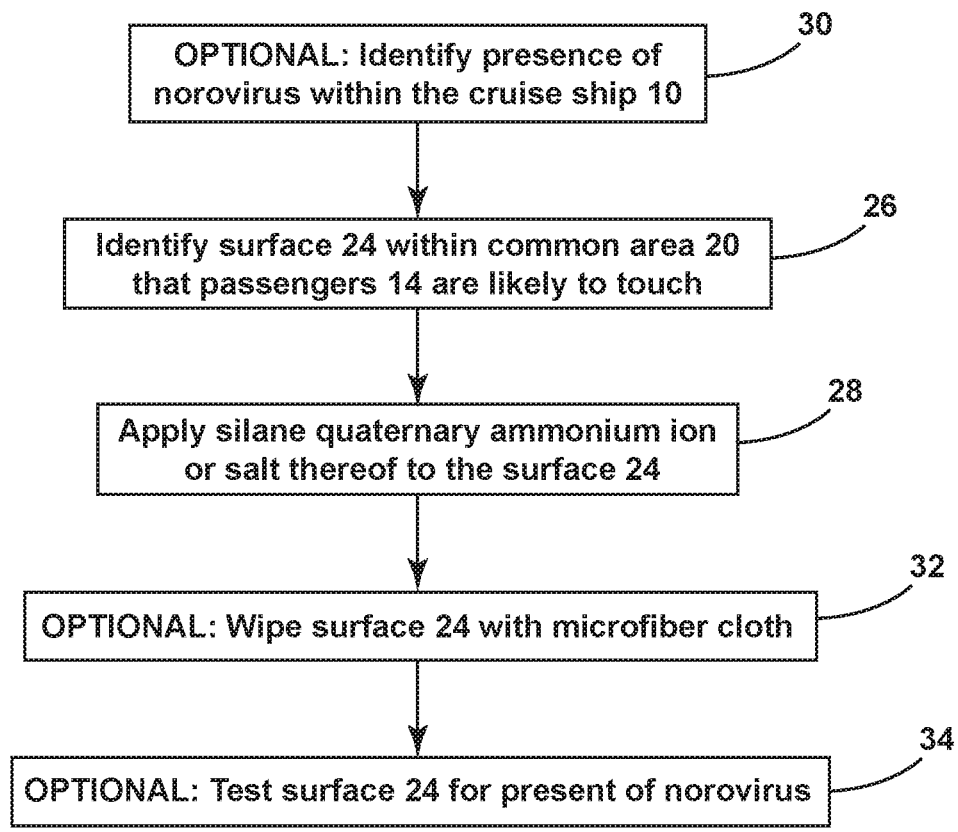
FIG. 8 is a flow chart illustrating a method of limiting the spread of norovirus within a cruise ship, including applying a quaternary ammonium ion or salt thereof to the surface of the common areas which passengers are likely to touch.

Referring now to FIG. 8, at step 26, a method of limiting the spread of norovirus within the cruise ship 10 comprises identifying a surface 24 within a common area 20 of a cruise ship 10 that passengers 14 are likely to touch. Examples of such surfaces 24 in such common areas 20 are provided above. A common area 20 could include any area to which many or all of the passengers 14 have access.

The method further includes, at step 28, applying a silane quaternary ammonium ion or salt thereof to the surfaces 24. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

Applying the silane quaternary ammonium ion or salt thereof to the surface can made by applying, to the surface 24, a solution including the silane quaternary ammonium ion or salt thereof and a solvent. The solvent can be isopropyl alcohol, among others. The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution. As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

The solution can be applied via spraying the solution containing the silane quaternary ammonium ion or salt thereof and the solvent with an electrostatic sprayer. Alternatively, the solution can be applied with a wipe soaked with the solvent, a spray bottle containing the solvent, and other means.

Quaternary ammonium compounds are generally thought to be ineffective in destroying non-enveloped viruses. The norovirus is a non-enveloped virus. Surprisingly, testing performed pursuant to ASTM E1053 has shown that a solution including 3-(trimethoxysilyl)propyldimethyloctadecyl ammonium chloride as the active ingredient was an effective virucidal solution against a norovirus-like virus. Because of difficulties in propagating norovirus, surrogate viruses which are able to be propagated in cell cultures have been discovered and used for testing purposes. The virus selected for the test was Bacteriophage MS2, which is a virus that infects *Escherichia coli*, and is an accepted surrogate virus for norovirus. Like norovirus, Bacteriophage MS2 is a non-enveloped virus.

For the testing, Petri dish carriers (a sufficient number for both test and control) were presented. The test Petri dish carriers were then sprayed five times with the solution including 3-(trimethoxysilyl)propyldimethyloctadecyl ammonium chloride as the active ingredient. The test Petri dish carriers were sprayed at a distance of between eight and ten inches and at an angle of 45 degrees. The solution was shaken before being sprayed. The test Petri dish carries with the solution applied thereon were then allowed to dry for fifty-eight minutes. The control Petri dish carriers were not sprayed with the solution including 3-(trimethoxysilyl)propyldimethyloctadecyl ammonium chloride as the active ingredient.

Both the test and control Petri dish carriers were then inoculated with the Bacteriophage MS2 virus. Specifically, the carriers were inoculated with 0.2 ml of the virus, which was spread of the entire surface area of the carrier (10-in$^2$). At time zero, the PFU/Carrier for the control carrier was measured at 9.25E+06. The carriers were then held for twenty-four hours.

Both the test and control carriers were neutralized and the level of the Bacteriophage MS2 virus remaining in each was determined. After the 24 hours holding time, the PFU/Carrier for the control carrier was 1.43E+06, and the PFU/Carrier for the test carrier was 2.95E+04. Thus, the login reduction compared to time zero was 0.81 for the control and 2.50 for the test (the carrier sprayed with the solution containing 3-(trimethoxysilyl)propyldimethyloctadecyl ammonium chloride as the active ingredient). The percent reduction compared to time zero was 84.6 percent for the control and 99.7 percent for the test. The $\log_{10}$ reduction for the test compared to the control was 1.68. The percent reduction for the test compared to the control was 97.9 percent. This testing surprisingly demonstrated that the solution containing 3-(trimethoxysilyl)propyldimethyloctadecyl ammonium chloride as the active ingredient satisfied the criteria for passing ASTM E1053, because a greater than 3-$\log_{10}$ reduction was observed in the test carrier compared to the control carrier.

The method can optionally further include, at step 30, identifying the presence of the norovirus within the cruise ship 10. Applying a silane quaternary ammonium ion or salt thereof to the surface 24 set forth above, to limit the spread of the norovirus within a cruise ship 10, can be performed either before the presence of the norovirus has been identified (as a preventative measure) or after the presence of norovirus has been identified (as a consequential measure to limit the spread of the norovirus and to reduce the amount of norovirus within the cruise ship to acceptable levels). The presence of the norovirus can be identified, for example, after an outbreak of sickness on the cruise ship 10. Documenting the existence of gastroenteritis among numerous passengers 14 of the cruise ship can give rise to the assumed identification of the norovirus within the cruise ship 10.

The method can optionally further include, at step 32, wiping the surface 24 with a microfiber cloth. If the solution including the silane quaternary ammonium ion or salt thereof has been applied to the surface 24 via spraying, then beads of the solution may develop on the surface 24. Wiping the surface 24 with a microfiber cloth spreads the solution and therefore the silane quaternary ammonium ion or salt thereof over the surface 24 more uniformly.

The method can optionally further include, at step 34, testing the surface 24 for the presence of the norovirus. After the solution including the silane quaternary ammonium ion or salt thereof has been applied to the surface 24, and after waiting a preset time (such as 24 hours), the surface 24 can be tested for the presence of the norovirus. Such testing can confirm that the silane quaternary ammonium ion or salt thereof applied to the surface 24 has effectively eliminated the norovirus from the surface 24. Alternatively, such testing can confirm whether another application of the silane quaternary ammonium ion or salt thereof to the surface 24 may be required to effectively eliminate the norovirus from the surface 24.

The invention claimed is:

1. A method of limiting spread of norovirus within a cruise ship comprising:
   documenting an existence of gastroenteritis among passengers of a cruise ship;
   identifying a surface within a common area of the cruise ship that passengers are likely to touch and spread norovirus; and
   applying, to the surface and to help prevent the spread of norovirus, a solution comprising a silane quaternary ammonium ion or salt thereof and isopropyl alcohol as solvent, the silane quaternary ammonium ion or salt being 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride;
   wherein, the isopropyl alcohol is between 55 percent and 65 percent by weight of the solution.

2. The method of claim 1 further comprising:
   wiping the surface with a microfiber cloth.

3. The method of claim 1 further comprising:
   testing the surface for presence of norovirus, after applying the solution, to confirm that the solution has effectively eliminated the norovirus from the surface.

4. The method of claim 1, wherein the common area is an elevator and the surface is an elevator button.

5. The method of claim 1, wherein the common area is a stairway and the surface is a handrail.

6. The method of claim 1, wherein the common area is a casino.

7. The method of claim 1, wherein the common area is a dining room.

8. The method of claim 1, wherein the common area is a walkway and the surface is a handrail.

9. The method of claim 1, wherein the solution is applied by spraying the solution onto the surface with an electrostatic sprayer.

10. The method of claim 1, wherein the silane quaternary ammonium ion or salt thereof is between 0.1 percent and 10 percent by weight of the solution.

11. The method of claim 10, wherein the silane quaternary ammonium ion or salt thereof is between 0.75 percent and 5 percent by weight of the solution.

12. The method of claim 11, wherein the silane quaternary ammonium ion or salt thereof is between 1.9 percent and 2.1 percent by weight of the solution.

13. The method of claim 1,
    wherein the step of applying, to the surface and to help prevent the spread of norovirus, the solution comprising the silane quaternary ammonium ion or salt thereof and isopropyl alcohol as the solvent comprises:
        applying, via spraying onto the surface with an electrostatic sprayer, the solution comprising:
            between 0.1 percent and 10 percent by weight 3-(trimethoxysilyl)propyldimethyloctadecyl ammonium ion or 3-(trimethoxysilyl)propyldimethyloctadecyl ammonium chloride.

14. The method of claim 13 further comprising:
    initially identifying presence of norovirus within the cruise ship;
    after spraying the solution onto the surface, wiping the surface with a microfiber cloth; and
    after wiping the surface with the microfiber cloth, waiting a preset period of time, and testing the surface for the presence of the norovirus;
    wherein, the common area is one of an elevator, a stairway, a casino, a dining room, or a walkway.

* * * * *

UNITED STATES PATENT AND TRADEMARK OFFICE
CERTIFICATE OF CORRECTION

PATENT NO. : 10,967,082 B2
APPLICATION NO. : 15/807157
DATED : April 6, 2021
INVENTOR(S) : Eddy It is certified that error appears in the above-identified patent and that said Letters Patent is hereby corrected as shown below:

In the Specification

Column 3, Line 31, after "can", insert --be--;

Column 4, Line 10, "carries" should be --carriers--;

Column 4, Line 19, "of" (1st occurrence) should be --on--; and

Column 4, Line 27, "login" should be --$\log_{10}$--.

Signed and Sealed this
Nineteenth Day of April, 2022

Katherine Kelly Vidal
*Director of the United States Patent and Trademark Office*